(12) United States Patent
Kramann

(10) Patent No.: US 10,004,522 B2
(45) Date of Patent: Jun. 26, 2018

(54) SNARE DEVICE FOR CATCHING AN OBJECT

(71) Applicant: PFM MEDICAL AG, Cologne (DE)

(72) Inventor: Bernhard Kramann, Homburg/Saar (DE)

(73) Assignee: PFM MEDICAL AG, Cologne (DE)

( * ) Notice: Subject to any disclaimer, the term of this patent is extended or adjusted under 35 U.S.C. 154(b) by 155 days.

(21) Appl. No.: 14/914,041

(22) PCT Filed: Aug. 28, 2014

(86) PCT No.: PCT/EP2014/068271
§ 371 (c)(1),
(2) Date: Feb. 24, 2016

(87) PCT Pub. No.: WO2015/028555
PCT Pub. Date: Mar. 5, 2015

(65) Prior Publication Data
US 2016/0199078 A1    Jul. 14, 2016

(30) Foreign Application Priority Data
Aug. 28, 2013  (DE) .................... 20 2013 103 881 U

(51) Int. Cl.
*A61B 17/24* (2006.01)
*A61B 17/221* (2006.01)
(Continued)

(52) U.S. Cl.
CPC ...... *A61B 17/221* (2013.01); *A61B 17/32056* (2013.01); *A61B 2017/00358* (2013.01);
(Continued)

(58) Field of Classification Search
CPC ............ A61B 17/221; A61B 17/32056; A61B 2017/00358; A61B 2017/2212;
(Continued)

(56) References Cited

U.S. PATENT DOCUMENTS 5,562,678 A    10/1996  Booker
5,697,128 A *  12/1997  Peregrine ................ F16G 11/14
                                                24/115 G
(Continued)

FOREIGN PATENT DOCUMENTS

DE         19514534        10/1996
DE         102006053448     6/2008
(Continued)

OTHER PUBLICATIONS

English translation of International Search Report from corresponding PCT application No. PCT/EP2014/068271 dated Oct. 31, 2014.

*Primary Examiner* — Katrina Stransky
*Assistant Examiner* — Kankindi Rwego
(74) *Attorney, Agent, or Firm* — Grossman, Tucker, Perreault & Pfleger, PLLC

(57) ABSTRACT

The invention relates to a snare device for catching an object, in particular for catching objects or foreign bodies in a human or animal body, said snare device comprising a hollow element, in particular a catheter, and a snare made of a flexible elastic shape-memory material, wherein the snare is movable relative to the hollow element and can be pulled into the hollow element and pushed out of it, and wherein the snare has an impressed original shape to which said snare return, when pushed out from the hollow element, as a result of the material stresses caused when it was pulled in, wherein the original shape of the snare has a twisted area, as a result of which a first loop and a second loop are formed, wherein the first loop is arranged substantially parallel to the longitudinal axis of the hollow element, and the second loop is at an angle with respect to the longitudinal axis of the hollow element, and which is characterized in that the snare thus deformed is introduced into the hollow element and is arranged inside the hollow element, in that the second loop is pivoted relative to the first loop and through the first loop, (Continued)

such that the second loop, on emerging from the hollow element, pivots back through the first loop as a result of the load being removed from the shape-memory material, thereby allowing the object to be enclosed.

9 Claims, 1 Drawing Sheet

(51) Int. Cl.
    *A61B 17/00*     (2006.01)
    *A61B 17/3205*     (2006.01)
    *A61B 17/22*     (2006.01)

(52) U.S. Cl.
    CPC ............... *A61B 2017/00867* (2013.01); *A61B 2017/00871* (2013.01); *A61B 2017/00902* (2013.01); *A61B 2017/2212* (2013.01); *A61B 2017/2217* (2013.01); *A61B 2017/22035* (2013.01)

(58) Field of Classification Search
    CPC .. A61B 2017/2217; A61B 2017/22034; A61B 2017/22035; A61B 2017/00867; A61B 2017/00871; A61B 17/22031; A61B 17/22032; F16G 11/14; F16G 11/146
    See application file for complete search history.

(56) References Cited

U.S. PATENT DOCUMENTS

| | | | |
|---|---|---|---|
| 2003/0005557 A1* | 1/2003 | Renn | B65D 63/10 24/115 G |
| 2012/0053596 A1* | 3/2012 | Gordon | A61B 17/221 606/127 |
| 2013/0184741 A1 | 7/2013 | Laroya et al. | |

FOREIGN PATENT DOCUMENTS

| | | | |
|---|---|---|---|
| EP | 1113755 | 12/2003 | |
| EP | 2052688 | 4/2009 | |
| WO | WO 0016703 A1 * | 3/2000 | ............ A61B 17/221 |

* cited by examiner

SNARE DEVICE FOR CATCHING AN OBJECT

CROSS-REFERENCE TO RELATED APPLICATION

This is the U.S. National Phase application under 35 U.S.C. § 371 of International Patent Application No. PCT/EP2014/068271 filed Aug. 28, 2014, which claims the benefit of German Patent Application No. 20 2013 103 881.4 filed on Aug. 28, 2013, both of them are incorporated by reference herein.

FIELD OF THE INVENTION

The invention relates to a snare device for catching an object, in particular for catching objects or foreign bodies in a human or animal body, said snare device comprising a hollow element, in particular a catheter, and a snare made of a flexible elastic shape-memory material, wherein the snare is movable relative to the hollow element and can be pulled into the hollow element and pushed out of it, and wherein the snare has an impressed original shape to which said snare returns, when pushed out from the hollow element, as a result of the material stresses caused when it was pulled in, wherein the original shape of the snare has a twisted area, as a result of which a first loop and a second loop are formed, wherein the first loop is arranged substantially parallel to the longitudinal axis of the hollow element, and the second loop is at an angle with respect to the longitudinal axis of the hollow element.

BACKGROUND

Snare devices for catching objects made of shape-memory material, which are kept in a hollow element and are movable relative to the hollow element are known in the prior art. In document DE 195 14 534 C2 and document EP 1 113 755 B1 snare devices are described, which enable the extraction of objects out of a human or animal body via a minimal invasive surgical intervention. These snare devices respectively show a snare formed by shape-memory material, which snare can be set around an object to be extracted. If the object to be extracted is placed in between the snare, the snare is tightened and the object can be extracted. With these snare devices it is possible to catch objects, in particular fragments of catheters or of guide wires out of many possible directions. The requirement is that the object can be enclosed by the snare. For this the object needs to offer an accessible end, over which end the snare can be placed, so that the object is probable. For catching objects which ends are not probable the known snare devices cannot be used.

Probable in the sense of the invention means that the snare of the snare device is put around an accessible end of the object to be caught. Afterwards the snare is tightened so that the object is enclosed by the snare. By a withdrawing of the snare device the object is finally extracted. The term "probable" is used in the following in the above mentioned matter.

Furthermore, document EP 2 052 688 B1 and document DE 10 2006 053 448 A1 describe snare devices, which have a locking wire wherein the locking wire can be pushed through the snare of the snare device to catch an object between a part of the snare and the locking wire extending through the loop. With these snare devices objects can be caught, which ends are not probable by putting the snare besides the object to be caught and the locking wire encloses the object on the opposite side of the object, wherein the locking wire engages into the loop and the object is caught between the snare and the locking wire. Thus the object is caught and can be extracted. It is disadvantageous by these snare devices that the hollow elements, which have to be used with the snare devices have a large diameter because said snare devices have in addition to the snare the interlocking wire.

At the daily clinical life situations occur relatively often, in which the ends of the objects to be extracted are non-probable. During around every tenth surgical intervention the aforementioned situation comes up. It can be tried to insert a pigtail-catheter separately and to hook with one end of said pigtail-catheter at the object, for instance a fragment of a catheter and to perform a pulling motion afterwards to that one end of the object is now probable, because the movement can lead to the situation that now the object is placed in an exposed area, for instance an adjacent vein or body cavities.

SUMMARY

For catching objects, which ends are not probable, special grippers built for the aforementioned application for the extraction of said objects respectively special built snare devices are known. These special instruments are exclusively for the application, that objects with non-probable ends need to be caught. These instruments have special hooks respectively hook-shaped snares, which can be used to hook the object and the object is then fixated by a locking wire. The locking wire is interlaced between the object and the hook-shaped snare so that the object is locked and can be extracted.

The solutions known from the prior art are disadvantageous, because these special instruments for catching objects with non-probable ends are only used, if the catching with conventional snare devices has failed. In the aforementioned case the conventional snare device has to be removed at a first step and in a second step the special instrument has to be inserted separately. This adds up to another disadvantage since the caliber of these special instruments is bigger/larger than the caliber of the conventional snare device. The diameter of the hollow element is distinctly larger, which can lead to complications at the puncture side. The consequences can be the development of thrombosis and/or of hardly stoppable secondary bleedings.

Based on the prior art it is the object of the invention to enhance the efficiency of the snare devices known from the prior art, in particular to provide the possibility to catch objects with probable ends and objects with non-probable ends with one snare device only.

It is another object of the invention to provide a snare device, which caliber is small even at the application when objects with non-probable ends need to be caught, in particular to avoid complications for the patient.

For the technical solution of the above mentioned object the invention at hand proposes a snare device named at the beginning, which is characterized in that the snare thus deformed is introduced into the hollow element and is arranged inside the hollow element, in that the second loop is pivoted relatively to the first loop and through the first loop, such that the second loop, on emerging from the hollow element, pivots back through the first loop as a result of the load being removed from the shape-memory material, thereby allowing the object to be enclosed.

The invention is based on the idea that a snare formed by shape-memory material of the aforementioned snare devices convent to the original form, if they are pushed out of the hollow element. Reasons for that is the result of the load put into the shape-memory material by putting the snare into the hollow element. If the snare is inserted into the hollow element in such a manner that the second loop is pivoted relatively to the first loop and through the first loop such that the second loop on emerging from the hollow element, it pivots back through the first loop to get back into the original form of the snare. By said pivot motion the object to be caught is enclosed. Objects, which ends are non-probable can be caught by using the inventive solution consequently and can be retrieved through the hollow element out of the human or animal body.

Advantageously the snare is introduced into the hollow element is such a way that the first loop is pivoted with respect to the second loop by about 270° and through the first loop and is arranged inside the hollow element elongated and pointing away from the distal outlet of the hollow element. This provides a sufficient pivot motion of the second loop so that the object to be caught can be completely enclosed respectively wrapped by the snare.

The snare formed out of shape-memory material of the inventive snare device is kept in a hollow element, in particular a catheter and movable relative to the hollow element. The deploying of the snare out of the catheter can be performed via an actuation apparatus by a surgeon. When exiting the distal end of the hollow element the snare deploys based on the material stresses in the shape-memory material. The snare can be completely pulled into the hollow element, if no object is grasped respectively enclosed by the snare.

The inventive snare device can be used at all vascular surgical interventions, for instance implantations of stents, endoscopic surgeries or for the treatment of cardio vascular diseases. The inventive snare device can be basically used for every surgery, which requires the catching and recovery of objects or foreign bodies in a human or animal body. According to the invention this is done by a minimally invasive surgical intervention.

Advantageously in the original shape of the snare the second loop is at an angle of about 90° with respect to the first loop. By such a configuration of the snare device an object to be caught can be grasped safely and easily with the snare. In particular it has to be ensured that the object to be caught is held safely so that it can be recovered through the hollow element.

In a further embodiment the first loop is larger than the second loop in the original shape of the snare. This substantially facilitates the back-pivoting of the second loop when the snare leaves the hollow element.

Advantageously the first loop is substantially triangular formed in the original shape of the snare. This further supports the back-pivoting of the second loop through the first loop. In a preferred embodiment the first loop of the snare has a bulge in the original shape, which facilitates the through-pivoting of the first loop through the second loop.

In an especially preferred embodiment the first loop and the second loop form an overlapping area in the original shape of the snare, in which overlapping area the object to be caught is supported during the enclosure by the snare. In order that the object to be caught does not affect the pivoting motion of the second loop of the snare, the object to be caught is supported between both loops in the overlapping area. The direct consequence of which is that the second loop is freely movable. The bulge of the first loop acts during the enclosure of the object to be caught by the loops of the snare like a hinge, wherein the object to be caught is trapped between both loops at the overlapping area during the back-pivoting of the second loop through the first loop. In such a manner it is ensured that the object is completely and safely enclosed so that a recovery through the hollow element is possible.

In a further embodiment the shape-memory material of the snare consists of metal, in particular of nitinol or of plastic.

Advantageously the hollow element has a diameter of about 2 to 8 French, preferred of about 4 to 6 French. Thus, the diameter of the hollow element, which is used with the snare device, is significantly smaller than the diameter of the special apparatuses for catching objects respectively foreign bodies, which ends are non-probable. A substantial advantage hereby is that complications at the puncture site by using hollow elements with larger diameters can be avoided. In particular the danger of thrombosis and/or hardly stoppable secondary bleedings at the puncture site are avoided.

The inventive snare device provides a marker to make the snare visible under displaying apparatuses. During the execution of a surgical intervention to recover an object or a foreign body it is advantageous if particularly the second loop provides a marker, which can be displayed under displaying apparatuses. This is achieved for instance by the usage of a fluoroscope, a MRT or further electronical displaying apparatuses, which display markers of the snare by using an x-ray device or a sonography. The markers can be for instance magnetic resonance markers.

Further details, features and advantages of the invention are described in the following by the embodiment shown in the figures.

DETAILED DESCRIPTION

Figure 1:
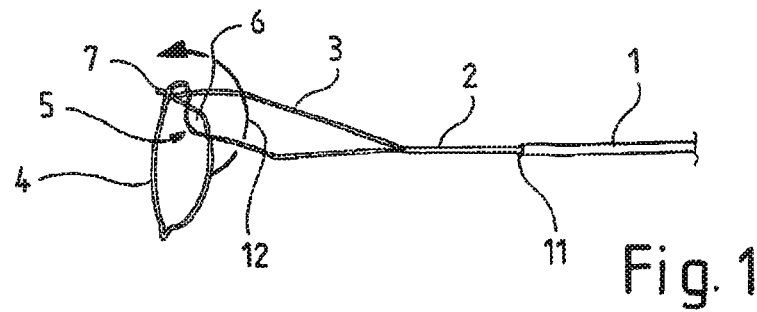
FIG. 1 an inventive snare device in the original form of the snare and pushed out of a catheter.

FIG. 1 shows an inventive snare device for catching of objects, in particular for catching of objects or foreign bodies in a human or animal body. The snare device has a catheter 1 and a snare. The snare is made of a flexible elastic shape-memory material, wherein the snare is movable relative to the catheter 1 and can be pulled into the catheter 1 and pushed out of it. Pushed out of the catheter the snare deploys into an impressed original shape. This happens during the pushing of the snare out of the catheter 1 as a result of the material stresses caused when it was pulled into the catheter 1. The snare has a first loop 3 and a second loop 4, which are connected to each other via a twisted area 7. At the distal end 11 of the catheter 1 the snare has a sheath 2. The first loop 3 is substantially triangular-shaped and forms together with the second loop 4 an overlapping area 6. Further, the first loop 3 has a bulge 5.

The snare is relatively movable to the catheter by pulling respectively pushing at the proximal end of the catheter. Thereto a surgeon can push respectively pull at the sheath 2 of the snare or push or pull at least a wire of the snare. Through this movement of the snare an object to be extracted is catchable. For extracting an object to be caught out of a human or animal body one pulls at the sheath 2 or at least one wire of the snare at the proximal end of the catheter 1. Through the pulling the snare is pulled at least partly into the catheter 1 and deformed so that the snare is tightening around the object to be caught. If the object to be caught is smaller than the opening of the used catheter 1, the object can be recovered through the catheter 1 respectively the object can be removed out of the human or animal body.

To catch an object according to the invention, for instance a fragment of a catheter, with non-probable ends it is required to change the original shape according to the presentation in FIG. 1 and to introduce the changed snare into the catheter 1. For this the second loop 4 is pivoted at an angle of about 270° relatively to the first loop 3 and through the first loop 3. This pivoting is shown in the figures by the arrow with the reference numeral 12. Thus, the first loop 3 and the second loop 4 are introduced in an elongated manner into the catheter 1. During the subsequent exiting of the snare the second loop 4 is attempted to get back into the original shape of the snare, displayed in FIG. 1 as a result of the load being removed from the shape-memory material. This only happens, when the second loop 4 pivots back through the triangular-shaped first loop 3. It has arisen that in some cases the object to be caught can interfere with the pivot motion of the second loop 4. To avoid this, the first loop 3 can have a bulge 5 and form an overlapping area 6 together with the second loop 4. The bulge 5 forms a niche, in which the object to be caught is supported. If the second loop 4 is pivoted back through the first loop 3, the object to be caught is pinched in the overlapping area 6. The bulge 5 acts like a hinge. The pivot motion of the second loop 4 is not obstructed by the object to be caught and the object can be enclosed.

Figure 2:
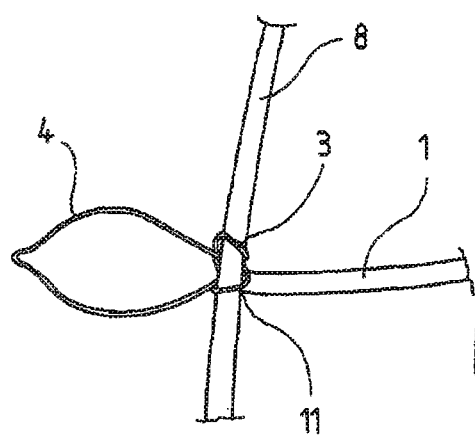
FIG. 2 the inventive snare device, which encloses an object to be caught with non-probable ends and FIG. 3 intracardiac positions of objects to be caught with non-probable ends, which show typical use cases for the inventive snare device.

In FIG. 2 an object 8 with non-probable ends is caught by the inventive snare device. After the catching the second loop 4 has a substantially oval shape. The first loop 3 is wrapped around the object 8. If the object 8 is enclosed by the snare, the distal end 11 of the catheter 1 is pushed forward, wherein the position of the object 8 remains the same. By pushing the catheter 1 forward the snare tightens around the object 8 and the object 8 can be extracted.

Figure 3:
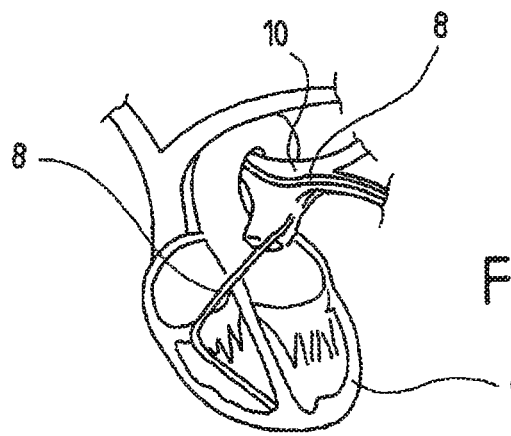

In FIG. 3 different positions of objects with non-probable ends are shown. These positions show typical use-cases for the inventive snare device. At hand an object 8 is arranged in the pulmonary artery 10 and is arranged in such a disadvantageous manner that the ends of the object 8 are non-probable. A comprehensible disadvantageous position of an object 8 to be caught is on hand if the object 8 is arranged in an intracardiac position in the heart 9. Then the ends of the object 8 to be caught are not probable, too. For these situations special instruments for the extraction were used in the past. According to the invention it is possible, like described above, to use the inventive snare device.

Advantageous the catheter used with the inventive snare device has a much smaller diameter than the catheters of the special instruments known from the prior art. Another advantage according to the invention at hand is that via the inventive snare device objects with probable ends can be caught as well. The usage of the snare device is then similar to the device and the method, with is described in document EP 2 052 688 B1.

The embodiments shown in the figures and which are described above are for the explanation of the invention solely and therefore non-restrictive for the invention.

REFERENCE NUMERALS 1 catheter
2 coating
3 first loop
4 second loop
5 bulge
6 overlapping area
7 twisted area
8 object
9 heart
10 pulmonary artery
11 distal end
12 pivoting

What is claimed is:

1. A snare device for catching an object or foreign body in a human or animal body, said snare device comprising:
   a hollow element comprising a catheter, and
   a snare made of a flexible elastic shape-memory material,
   wherein the snare is movable relative to the hollow element and is pullable into the hollow element and is pushable out of the hollow element, and
   wherein the snare has an impressed original shape to which said snare returns, when pushed out of the hollow element, as a result of material stresses caused when the snare was earlier introduced into the hollow element,
   wherein the original shape of the snare has a twisted area, as a result of which a first loop and a second loop are formed,
   wherein the first loop is arranged substantially parallel to a longitudinal axis of the hollow element, and the second loop is at an angle with respect to the longitudinal axis of the hollow element,
   wherein the snare thus deformed is introduced into the hollow element and is arranged inside the hollow element, in that the second loop is pivoted relative to the first loop and through the first loop, such that the second loop, on emerging from the hollow element, pivots back through the first loop as a result of the load being removed from the shape-memory material, thereby allowing the object to be enclosed.

2. The snare device as claimed in claim 1, wherein, in the original shape of the snare, the second loop is at an angle of about 90° with respect to the first loop.

3. The snare device as claimed in claim 1, wherein, in the original shape of the snare, the first loop is larger than the second loop.

4. The snare device as claimed in claim 1, wherein, in the original shape of the snare, the first loop is substantially triangular formed.

5. The snare device as claimed in claim 1, wherein, in the original shape of the snare, the first loop has a bulge, which facilitates the through-pivoting of the first loop through the second loop.

6. The snare device as claimed in claim 1, wherein, in the original shape of the snare, the first loop and the second loop form an overlapping area, in which overlapping area the object to be caught is supported during the enclosure by the snare.

7. The snare device as claimed in claim 1, wherein the shape-memory material of the snare is formed of shape-memory metal or plastic.

8. The snare device as claimed in claim 1, wherein the hollow element has a diameter of about 2 to 8 French.

9. The snare device as claimed in claim 1, wherein the snare includes a marker to make the snare visible under a displaying apparatus.

* * * * *